United States Patent
Schultz et al.

(10) Patent No.: US 8,980,596 B2
(45) Date of Patent: *Mar. 17, 2015

(54) FERMENTATION AND SIMULATED MOVING BED PROCESS

(71) Applicant: LanzaTech New Zealand Limited, Auckland (NZ)

(72) Inventors: Michael Anthony Schultz, Roselle, IL (US); Alice Marie Havill, Auckland (NZ); Anil R Oroskar, Oak Brook, IL (US)

(73) Assignee: LanzaTech New Zealand Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 13/901,455

(22) Filed: May 23, 2013

(65) Prior Publication Data

US 2013/0316412 A1    Nov. 28, 2013

Related U.S. Application Data

(60) Provisional application No. 61/650,655, filed on May 23, 2012.

(51) Int. Cl.
    *C12P 7/18* (2006.01)
    *C12P 7/06* (2006.01)
    (Continued)

(52) U.S. Cl.
    CPC ... *C12P 7/06* (2013.01); *C12P 7/18* (2013.01); *Y02E 50/17* (2013.01); *C12M 21/12* (2013.01);
    (Continued)

(58) Field of Classification Search
    CPC ........... C12P 19/14; C12P 19/18; C12P 7/18; C12P 13/06; C12P 19/26; C12P 7/16; C12P 7/06; C12P 7/56; C12P 41/009; C12P 7/54; C12P 19/02; C12P 7/065; C12P 7/08; C12P 7/10; C12P 7/20; C12P 7/46; C12P 7/62; C12N 15/52; C12N 9/1074; Y02E 50/17; Y02E 50/10; Y02E 50/13; Y02E 50/16; Y02E 50/343

See application file for complete search history.

(56) References Cited

U.S. PATENT DOCUMENTS 4,319,058 A * 3/1982 Kulprathipanja et al. .... 568/917
4,333,740 A   6/1982 Priegnitz
(Continued)

FOREIGN PATENT DOCUMENTS

EP  117309       9/1984
EP  07706766 A2 * 5/1997
(Continued)

OTHER PUBLICATIONS

Kopke et al., Appl. Environ. Microbiol. 77(15): 5467-5475 (2011).*
(Continued)

*Primary Examiner* — Patricia A Leith
*Assistant Examiner* — Erin M Bowers
(74) *Attorney, Agent, or Firm* — Frank S Molinaro (57) ABSTRACT

The invention provides an improved method for the production, separation and recovery of one or more fermentation products from a fermentation broth. Further, the invention provides a method for increasing efficiency of a fermentation reaction. In particular, the invention relates to a fermentation system which incorporates a simulated moving bed for separation of fermentation products from a fermentation broth, and a corresponding method.

7 Claims, 2 Drawing Sheets

(51) Int. Cl.
*C12M 1/00* (2006.01)
*C12P 7/08* (2006.01)
*C12P 7/16* (2006.01)
*C12P 7/54* (2006.01)

(52) U.S. Cl.
CPC ............... *C12M 47/10* (2013.01); *C12P 7/065* (2013.01); *C12P 7/08* (2013.01); *C12P 7/16* (2013.01); *C12P 7/54* (2013.01); *Y02E 50/10* (2013.01)
USPC .......................................... 435/158; 435/161

(56) References Cited

U.S. PATENT DOCUMENTS

| | | | |
|---|---|---|---|
| 5,173,429 | A | 12/1992 | Gaddy et al. |
| 5,593,886 | A | 1/1997 | Gaddy |
| 5,807,722 | A | 9/1998 | Gaddy |
| 5,821,111 | A | 10/1998 | Gaddy |
| 6,136,577 | A | 10/2000 | Gaddy |
| 6,340,581 | B1 | 1/2002 | Gaddy |
| 6,368,819 | B1 | 4/2002 | Gaddy et al. |
| 8,658,845 | B2 * | 2/2014 | Oroskar et al. ............... 568/913 |
| 2005/0222482 | A1 | 10/2005 | Lee et al. |
| 2006/0251762 | A1 | 11/2006 | Jansen et al. |
| 2010/0105115 | A1 * | 4/2010 | Simpson et al. ............. 435/135 |
| 2010/0323417 | A1 | 12/2010 | Simpson et al. |
| 2011/0059499 | A1 * | 3/2011 | Simpson et al. ............. 435/161 |
| 2011/0229947 | A1 | 9/2011 | Zahn et al. |

FOREIGN PATENT DOCUMENTS

| | | |
|---|---|---|
| GB | 2416776 | 2/2006 |
| WO | WO 98/00558 | 1/1998 |
| WO | WO 00/68407 | 11/2000 |
| WO | WO 02/08438 | 1/2002 |
| WO | WO2007/117157 | 10/2007 |
| WO | WO 2008/028055 | 3/2008 |
| WO | WO2008/115080 | 9/2008 |
| WO | WO2009/022925 | 2/2009 |
| WO | WO2009/064200 | 5/2009 |
| WO | WO2009/151342 | 12/2009 |
| WO | WO 2010093262 | 8/2010 |
| WO | WO2012/024522 | 2/2012 |
| WO | WO2012/131627 | 10/2012 |

OTHER PUBLICATIONS

Roshchina et al., Protection of Metals 44(2): 174-179 (2008).*
Syu MJ, Appl Microbiol Biotechnol 55:10-18 (2001).
Qin et al., Chinese J Chem Eng 14(1):132-136 (2006).
Abrini J, Naveau H, Nyns E-J: *Clostridium* autoethanogenum, sp. nov., an anaerobic bacterium that produces ethanol from carbon monoxide. Arch Microbiol 4: 345-351 (1994).
Liou et al., International Journal of Systematic and Evolutionary Microbiology 55: pp. 2085-2091 (2005).
Sakai et al, Biotechnology Letters 26: pp. 1607-1612 (2004).
Svetlichny, V.A., Sokolova, T.G. et al , Systematic and Applied Microbiology 14: 254-260(1991).
Simpa et. al. Critical Reviews in Biotechnology, vol. 26. pp. 41-65 (2006).
Tanner RS, Miller LM, Yang D: *Clostridium ljungdahlii* sp. nov., an Acetogenic Species in Clostridial rRNA Homology Group I. Int J Syst Bacteriol , 43: 232-236 (1993).
Tirado-Acevedo O. Production of Bioethanol from Synthesis Gas Using *Clostridium ljungdahlii*. PhD thesis, North Carolina State University, 2010.
Wu, J. et al., Model-based design of a pilot-scale simulated moving bed for purification of citric acid from fermentation broth, Chromatography A, (2009), pp. 8793-8805.
Australian Paten Exam Report No. 1; Mar. 7, 2014.

* cited by examiner

FERMENTATION AND SIMULATED MOVING BED PROCESS

FIELD OF THE INVENTION

This invention relates generally to a system and a method for producing products, particularly alcohols, by microbial fermentation. In particular, the invention relates to a fermentation system which incorporates a simulated moving bed for separation of fermentation products from a fermentation broth, and a corresponding method.

BACKGROUND OF THE INVENTION

Biofuels for transportation are attractive replacements for gasoline and are rapidly penetrating fuel markets as low concentration blends. Biofuels, derived from natural sources, are more environmentally sustainable than those derived from fossil resources (such as gasoline), their use allowing a reduction in the levels of so-called fossil carbon dioxide ($CO_2$) gas that is released into the atmosphere as a result of fuel combustion. In addition, biofuels can be produced locally in many geographical areas, and can act to reduce dependence on imported fossil energy resources.

Ethanol is rapidly becoming a major hydrogen-rich liquid transport fuel around the world. Worldwide consumption of ethanol was expected to reach 27.2 billion gallons by 2012 and the global market for the fuel ethanol industry has also been predicted to grow sharply in future. This growth is mainly due to an increased interest in ethanol in Europe, Japan, the USA and several developing nations.

For example, in the USA, ethanol is used to produce E10, a 10% mixture of ethanol in gasoline. In E10 blends, the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

Butanediols including 1,2-butanediol, 1,3-butanediol, 1,4-butanediol and 2,3-butanediol may be used as an automotive fuel additive. They may also be relatively easily transformed into a number of other potentially higher value and/or higher energy products. For example, 2,3-butanediol may be readily converted in a two step process into an eight-carbon dimer which can be used as aviation fuel.

2,3-Butanediol derives its versatility from its di-functional backbone, i.e., 2 hydroxyl groups are located at vicinal C-atoms allowing the molecule to be transformed quite easily into substances such as butadiene, butadione, acetoin, methylethyl ketone etc. These chemical compounds are used as base molecules to manufacture a vast range of industrially produced chemicals.

In addition, 2,3-butanediol may be used as a fuel in an internal combustion engine. It is in several ways more similar to gasoline than it is to ethanol. As the interest in the production and application of environmentally sustainable fuels has strengthened, interest in biological processes to produce 2,3-butanediol (often referred to as bio-butanol) has increased.

The vast majority of fuel ethanol is produced via traditional yeast-based fermentation processes that use crop derived carbohydrates, such as sucrose extracted from sugarcane or starch extracted from grain crops, as the main carbon source. 2,3-Butanediol can also be produced by microbial fermentation of carbohydrate containing feedstock (Syu M J, *Appl Microbiol Biotechnol* 55:10-18 (2001), Qin et al., *Chinese J Chem Eng* 14(1):132-136 (2006)). However, the cost of these carbohydrate feed stocks is influenced by their value as human food or animal feed, while the cultivation of starch or sucrose-producing crops for ethanol production is not economically sustainable in all geographies. Therefore, it is of interest to develop technologies to convert lower cost and/or more abundant carbon resources into biofuel products.

Carbon monoxide (CO) is a major free energy-rich by-product of the incomplete combustion of organic materials such as coal or oil and oil derived products. For example, the steel industry in Australia is reported to produce and release into the atmosphere over 500,000 tonnes of CO annually.

It has long been recognised that catalytic processes may be used to convert gases consisting primarily of CO and/or CO and hydrogen ($H_2$) into a variety of fuels and chemicals. However, micro-organisms may also be used to convert these gases into fuels and chemicals. These biological processes, although generally slower than chemical reactions, have several advantages over catalytic processes, including higher specificity, higher yields, lower energy costs and greater resistance to poisoning.

The ability of micro-organisms to grow on CO as their sole carbon source was first discovered in 1903. This was later determined to be a property of organisms that use the acetyl coenzyme A (acetyl CoA) biochemical pathway of autotrophic growth (also known as the Woods-Ljungdahl pathway). A large number of anaerobic organisms including carboxydotrophic, photosynthetic, methanogenic and acetogenic organisms have been shown to metabolize CO to various end products such as $CO_2$, $H_2$, methane, n-butanol, acetic acid and ethanol.

Anaerobic bacteria, such as those from the genus *Clostridium*, have been demonstrated to produce ethanol from CO, $CO_2$ and $H_2$ via the acetyl CoA biochemical pathway. For example, various strains of *Clostridium ljungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Abrini et al, *Archives of Microbiology* 161, pp 345-351 (1994)).

However, biofuel production by micro-organisms by fermentation of gases is always associated with co-production of acetate and/or acetic acid as a by-product. This acetate/acetic acid has the potential to inhibit the reaction and is normally required to be removed from the fermentation broth. Also, unless the acetate/acetic acid by-product can be used for some other purpose, it may pose a waste disposal problem. Acetate/acetic acid is converted to methane by micro-organisms and therefore has the potential to contribute to Green House Gas (GHG) emissions.

Fermentation of gaseous substrates to produce products such as ethanol and 2,3-butanediol is typically carried out in a bioreactor containing a liquid fermentation broth. The broth contains microorganisms and nutrients for their growth. Over time, the nutrients (including the gaseous substrate itself) are converted to desirable products but undesirable by-products and cell debris are also produced that may be toxic to the microorganism. Both desirable and undesirable products may inhibit fermentation efficiency, particularly when present in high concentrations.

In order to recover desirable products and reduce reaction inefficiencies brought about by inhibition of the fermentation reaction, the broth is removed from the bioreactor in a continuous or batch process and replaced with fresh nutrient medium. The desirable products are typically extracted from the broth by way of standard extraction methods such as fractional distillation and extractive fermentation. However, these known methods for extracting organic metabolites from fermentation solutions suffer a number of problems.

Solvent extraction systems often exhibit poor partition ratios when applied to weak organic broths thus making separation difficult. Salt saturation can improve the partition ratios but complicates the extraction process by requiring the removal of the salts from the waste aqueous and dramatically increases consumable costs if the salts cannot be recovered for reuse. Liquid pressure membranes (such as Reverse Osmosis and nanofiltration membranes) do not show sufficiently high rejection for short chained alcohols, diols, and organic acids. Neither hydrophobic nor hydrophilic membranes can be manufactured with tight enough molecular weight cut-offs to exhibit clear separation and both membrane types show severe particulate fouling in fermentation broths, requiring rigorous pre-filtration.

Distillation is currently the primary method for continuous, high purity organic recovery. However, distillation is limited to being used with organic products with lower boiling points than water and without unfavorable azeotropes. Separation of 2,3-butanediol from an aqueous solution by distillation is costly and difficult due to the high boiling point of 2,3-butanediol (180-184° C.) and high affinity of water. Distillation of ethanol from a fermentation broth yields an azeotropic mixture of ethanol and water (i.e. 95% ethanol and 5% water) that cannot be resolved by distillation and requires further steps and technology to separate effectively.

Acetic acid is typically removed by filtration of the broth to remove suspended organic matter followed by passing the broth through an activated charcoal column to adsorb the acetate. This process requires that the pH of the fermentation broth is reduced to less than about 3 before it is passed through the activated charcoal column, to convert the majority of the acetate to the acetic acid form. This method of removal is undesirable as it requires further steps and the addition of pH modifying chemicals to the broth.

Known methods of product recovery are often not appropriate (or are inefficient, in terms of costs and/or energy consumption and/or proprotion of product recovered) to recover major classes of organic products that can be manufactured through fermentation systems, including 2,3-butanediol and acetic acid. Recovery is therefore a bottle-neck for commercially viable production of biofuels using microbial fermentation and there is a need for novel technologies to improve recovery in a more efficient and cost-effective manner.

It is an object of the present invention to provide a process and a fermentation system that overcomes or ameliorates at least one of the disadvantages of the prior art, or at least to provide the public with a useful choice.

SUMMARY OF THE INVENTION

The invention relates to methods for improving the efficiency of separation of one or more fermentation products from a fermentation broth. The invention provides a method for the separation of one or more fermentation products from a fermentation broth, wherein the energy requirement for the separation is substantially reduced compared to known methods.

The invention further provides an improved method of separation of one or more fermentation products from a fermentation broth by providing an improved system for the removal of water from the fermentation stream comprising the one or more fermentation products.

In a first aspect, the invention provides a method of separation of one or more fermentation products from a fermentation broth, the method comprising:
a) fermenting a gaseous substrate in a bioreactor containing a culture of one or more microorganisms to produce a fermentation broth comprising the one or more fermentation products;
b) passing the fermentation broth through a treatment zone operated at conditions to produce a treated broth stream, said treated broth stream being substantially free of biomass;
c) providing at least a portion of the treated broth stream to a simulated moving bed (SMB) module comprising an adsorbent;
d) adsorbing the one or more fermentation products onto said adsorbent and yielding a raffinate containing the non-adsorbed components of the broth; and
e) desorbing the one or more products from the adsorbent to yield a product stream.

In one embodiment of the first aspect, the treatment zone comprises at least a heat treatment zone. In one embodiment of the first aspect, the treatment zone comprises a heat treatment zone and a filtration zone. In one embodiment, the treatment zone removes at least a portion of suspended and/or soluble biomass from the fermentation broth. In one embodiment, the treatment zone removes substantially all of the suspended and or soluble biomass form the fermentation broth. In certain aspects of the invention the treated broth stream is substantially free of biomass. In certain embodiments, the treated broth stream may contain trace amounts of biomass.

In one embodiment of the first aspect, the method comprises the step of recycling the raffinate to the bioreactor.

In a further embodiment of the first aspect, the products are desorbed in step (e) by flushing the adsorbent with a solvent to yield a product-solvent solution. Preferably the product-solvent solution is substantially free of salts carried over from the fermentation broth. Preferably the concentration of water in the product-solvent solution is less than 5%/vol, or less than 3%/vol, or less than 1%/vol. In one embodiment there is substantially no water in the product-solvent solution.

Preferably, the products include acids and/or alcohols. In certain embodiments the solvent is an alcohol. According to one embodiment, the products are selected from the group comprising ethanol, acetic acid, 2,3-butanediol, butanol, isopropanol and acetone. In one embodiment the solvent is selected from the group comprising ethanol, methanol, propanol and methyl tertiary butyl ether. In a preferred embodiment the one or more products is selected from the group comprising ethanol, 2,3-butanediol and acetic acid, and the solvent is ethanol.

In one embodiment the solvent used in the desorbtion step, is a product of the fermentation process that has been previously extracted. It will be appreciated that desorbing with a product of the fermentation process means that a further required separation stage is not added to yield the products although further separation may be required to separate the different products of the fermentation from one another where more than one product is produced.

In a particular embodiment, the gaseous substrate is fermented in the bioreactor in step (a) to produce a fermentation broth comprising ethanol and 2,3-butanediol. The fermentation broth is passed to a treatment zone, wherein at least a portion of biomass and/or soluble proteins is removed from the fermentation broth to provide a treated stream. In a particular embodiment, the treated stream is flowed to the SMB, wherein at least a portion of the ethanol and 2,3-butanediol is absorbed from the treated stream to yield a raffinate stream. A solvent is passed through the adsorber to desorb the ethanol and 2,3-butanediol and provide an extract stream. In a further embodiment, the extract stream is passed to a recovery zone operated under conditions to provide an ethanol stream and a 2,3-butanediol stream. In a particular embodiment, at least a portion of the raffinate stream is passed back to the bioreactor.

In a second aspect, the invention provides a method for the production and recovery of one or more fermentation products from a fermentation broth, the method comprising;
  a) fermenting a gaseous substrate in a bioreactor containing a culture of one or more microorganisms to produce a fermentation broth comprising the one or more fermentation products;
  b) passing the fermentation broth through a treatment zone operated at conditions to produce a treated broth stream, said treated broth stream being substantially free of biomass;
  c) providing at least a portion of the treated broth stream to a simulated moving bed (SMB) module comprising an adsorbent;
  d) adsorbing the one or more fermentation products onto said adsorbent and yielding a raffinate containing the non-adsorbed components of the broth;
  e) desorbing the one or more products from the adsorbent to yield a product stream; and
  f) recycling at least a portion of the raffinate to the bioreactor.

In one embodiment of the invention, the treatment zone of step (b) removes at least a portion of biomass and/or soluble proteins from the fermentation broth to provide a treated broth stream substantially free of biomass. In one embodiment, at least a portion of the biomass and/or soluble proteins is returned to the bioreactor.

In one embodiment of the invention, at least a portion of the fermentation broth is passed through a filtration step as it exits the bioreactor, producing a permeate stream. In certain embodiments, the permeate stream and treated broth streams are combined prior to being passed to the SMB module.

In one embodiment, the raffinate is returned to the bioreactor to make up a portion of a liquid nutrient medium. In certain embodiments, the raffinate passes through a media preparation step prior to being returned to the bioreactor. In certain embodiments, the media preparation step comprises the addition of one or more nutrients to the raffinate stream.

In certain embodiments the raffinate is substantially free of products. In preferred embodiments the raffinate comprises at least 80% H2O, or at least 85% H2O, or at least 90% H2O, or at least 95% H2O. In certain embodiments the raffinate comprises trace amounts of the solvent used to desorb the one or more products from the adsorber.

In a third aspect there is provided a method for the production and recovery of one or more acids, the method comprising;
  a) flowing a gaseous substrate to a bioreactor containing a culture or one or more microorganisms in a liquid nutrient broth;
  b) fermenting the gaseous substrate to produce a fermentation broth comprising one or more acid(s);
  c) passing the fermentation broth to a treatment zone, wherein at least a portion of biomass and/or soluble proteins is removed from the fermentation broth to provide a treated broth stream;
  d) flowing the treated broth stream to a Simulated Moving Bed module comprising an adsorbent;
  e) adsorbing at least a portion of the one or more acids from the treated broth stream to the adsorbent to yield a raffinate stream;
  f) passing a solvent through the adsorber to desorb the one or more acids; and
  g) passing at least a portion of the raffinate stream back to the bioreactor.

In one embodiment of the third aspect, the acid adsorbed is lactic acid and/or acetic acid and the removal of the acid prevents inhibition and/or collapse of the broth culture. In a particular embodiment, the adsorbed lactic acid and/or acetic acid is desorbed from the absorbent and exits the SMB through the extract stream. Accordingly, the pH of the broth is controlled through removal of the lactic acid and/or acetic acid through the extract stream. In one embodiment, the removal of the acid from the bioreactor prevents inhibition of the culture of one or more microorganisms.

In one embodiment, the one or more acid(s) are desorbed in step (f) by a solvent. According to one embodiment, the solvent used for desorbing is ethanol, methanol, propanol and methyl tertiary butyl ether. In a further embodiment, the solvent used for desorbing is a solvent produced by the fermentation process that has been previously extracted.

In an alternative embodiment of the third aspect, at least a portion of acid in the treated broth stream is converted to its corresponding salt prior to being provided to the SMB module. In one embodiment, the acid of the treated broth stream is acetic acid which is converted to sodium acetate using sodium hydroxide. The converted sodium acetate is provided with the treated broth stream to the SMB module, wherein the sodium acetate exits the SMB module with the raffinate and is recycled back to the bioreactor.

In one embodiment, the biomass and/or soluble proteins removed from the fermentation broth at step (c) are recycled to the bioreactor.

In one embodiment of the third aspect, one or more acids are removed by the process such that the pH of the bioreactor is maintained within a desirable range. It has been recognised that microbial growth and metabolite production can be optimised by maintaining the pH in the bioreactor within a desirable range. In a particular embodiment, the desirable range is ±0.5 units of the optimum operating pH. Typically, in an acetic acid fermentation, the pH is maintained between 6-8, or between 6.5-7.5, or between 6.7-7.4, or between 6.8-7.3, or between 6.9-7.1, or substantially 7.0. In fermentations according to aspects 1 and 2 of the invention, the pH is maintained between 4.5-6; or between 4.61-5.9; or within 4.7-5.8; or between 4.8-5.5 In one embodiment the pH is maintained at substantially pH4.8, or at pH 5.0, or at pH5.5

In certain embodiments of the third aspect, the main fermentation product is acetic acid. In certain embodiments the gaseous substrate provided to the reactor is selected from the group consisting of CO, CO and H2, CO2 and H2, CO2, CO and H2, or mixtures thereof. In one embodiment of the third aspect, the one or more microorganisms is selected from the group consisting of *Acetobacterium woodii*, *Clostridium autoethanogenum*, *Clostridium ljungdahlii*, *Clostridium ragsdalei*, *Clostridium coskatii* or mixtures thereof.

Step (a) of the third aspect may produce other products also, such as alcohols. In a particular embodiment, one or more additional fermentation products are adsorbed in step (e). According to one embodiment, the additional products are selected from the group comprising ethanol, 2,3-butanediol, butanol, and iso-propanol.

In a particular embodiment of any of the above aspects, the treatment stage comprises at least a filtration step wherein at least a portion of suspended and/or soluble biomass is removed from the fermentation broth prior to passing it to the SMB module. Filtration results in the removal of suspended and/or soluble biomass from the fermentation broth. In certain embodiments, filtration results in a substantially biomass free treated broth stream. Filtration may be by way of passing the broth through a membrane. In one embodiment flocculation can be induced by the addition of a flocculent prior to filtration.

In certain embodiments, the treatment stage further comprises a least a heat treatment stage. It would be appreciated by a skilled person that other methods for removal of biomass from a broth stream can also be used in the treatment stage.

It will be appreciated that performance of the method of the first aspect may result in performance of the method of the second aspect and vice versa.

In a further aspect, the invention provides a fermentation system comprising at least:
 a) a bioreactor containing a fermentation broth containing a culture of one or more microorganisms able to produce one or more fermentation products from a gaseous substrate;
 b) a simulated moving bed (SMB) module adapted to be provided with a portion of the fermentation broth;
 c) an adsorbent in the SMB module adapted to adsorb the one or more fermentation products from the portion of the fermentation broth.

In one embodiment, the system further comprises a treatment module adapted to remove suspended and/or soluble biomass from the portion of the fermentation broth prior to the broth being received by the SMB module. The treatment module comprises at least a filtration module. In certain embodiments the treatment module comprises a heat treatment module and a filtration module. As indicated previously, the SMB module may be provided in or as part of the bioreactor or separate therefrom but in fluid communication therewith so as to receive the portion of the broth.

In one embodiment, the system further comprises a means for passing the removed biomass/soluble proteins back to the bioreactor. In one embodiment, the system comprises a means for passing a raffinate stream exiting the SMB module back to the bioreactor.

In particular embodiments of the third aspect, the bioreactor is configured for fermentation of a gaseous substrate to produce products including acid(s) and/or alcohol(s). In a particular embodiment, the gaseous substrate comprises CO and optionally $H_2$. In alternative embodiments, the gaseous substrate comprises $CO_2$ and $H_2$.

In particular embodiments of the third aspect, the system includes control means and processing means such that parameters including media supply rates, liquid retention times and substrate supply rates can be controlled in accordance with the instant disclosure and methods known in the art, such as methods described in WO2010/093262, which are fully incorporated herein by reference.

In a particular embodiment of any of the above aspects, the method further comprises the treatment of the fermentation broth removed from the bioreactor or the raffinate respectively prior to or after product removal in the SMB module. In particular embodiments, the treatment may consist of additional components or nutrients (such as B vitamins) being added to the raffinate to replenish the nutrient medium before it is returned to the bioreactor. Also, the pH of the raffinate may be adjusted before being returned to the bioreactor to control the pH of the broth in the bioreactor.

In a particular embodiment of any of the above aspects, the adsorbent is a fluorinated carbon adsorbent. In alternative embodiments the adsorbent is an activated carbon adsorbent. In other embodiments the adsorbent is a C18 surface modified silica gel.

The above mentioned adsorbents are examples of suitable adsorbents and are not intended as an exhaustive list. A skilled person would understand that any adsorbent material having suitable selectivity and hydrophobicity for use in the SMB process defined herein may be used.

While it is preferred that the SMB is separate from but in fluid communication with the bioreactor, the SMB may be provided within the bioreactor. Where the SMB is included within the bioreactor, preferably, the SMB is kept separate from suspended and/or soluble biomass in the broth. For example, a portion of the broth may be separated from the rest by a membrane such that the SMB is in communication with products of the fermentation but not suspended or soluble biomass which can affect the performance of the SMB. Additionally or alternatively, a feed of the SMB may be provided with a filter there over to the same end. This applies to all aspects of the invention.

Surprisingly it was found that the SMB process is advantageous in separating desired products from a fermentation broth and/or treated broth stream comprising dilute concentrations of organic products. In one embodiment of the invention, the concentration of ethanol and/or 2,3-butanediol in the fermentation broth and treated broth stream is less than or equal to 30 weight % in water, or less than 15 weight % in water. In one embodiment, the fermentation broth or treated stream contains between 2-10 weight % of ethanol/2,3-butanediol in water, wherein the ethanol to 2,3-butanediol is present at a ratio between 5:1 to 1:1. In a preferred embodiment, the fermentation broth or treated stream contains 6 weight % of ethanol/2,3-butantediol in water, wherein the ethanol to 2,3-butanediol is present at a ratio of 1:1. Further, it was surprisingly found that a 2,3-butanediol concentration of less than 2 weight % may be separated using the SMB process. In a particular embodiment, the adsorbent adsorbs at least approximately 50%, approximately 60%, approximately 70%, approximately 80%, approximately 90%, approximately 95%, approximately 99% or substantially 100% of the fermentation products from the broth. In one embodiment the adsorbent adsorbs between 50-100%, or between 60-95%, or between 70-90%, or between 70-100% of the fermentation products from the broth.

In particular embodiments of the invention, the adsorbent would preferably have an ethanol adsorption ratio of at least 6.0 W/W, or at least 7.0 W/W, or at least 8.0 W/W, or at least 9.0 W/W, or at least 10.0 W/W. In certain embodiments, the adsorbent has an ethanol adsorption ratio of between 6.0-10.0 W/W, or between 7.0-10.0 W/W, or between 6.0-9.0 W/W, or between 7.0-9.0 W/W.

In accordance with the invention, the adsorbent would preferably have a 2,3-butanediol adsorption ratio of at least 9.0 W/W, or at least 10.0 W/W, or at least 12.0 W/W, or at least 16.0 W/W, or at least 18.0 W/W, or at least 20.0 W/W. In certain embodiments the adsorbent has a 2,3-butanediol adsorption ratio of between 9.0-20.0 W/W, or between 12.0-20.0 W/W, or between 10.0-18.0 W/W, or between 12.0-18.0 W/W, or between 16.0-20.0 W/W.

In a particular embodiment of the invention, the temperature at which the organic products are adsorbed to the adsorbent is between 20° C. to 75° C., or between 25° C. to 40° C., or between 25° C.- to 35° C. In a preferred embodiment the temperature at which the organic products are adsorbed to the adsorbent is about 25° C. As will be appreciated, this is significantly less than that required to separate the products by distillation.

In certain embodiments of the invention, the temperature at which the products are desorbed from the adsorbent is less between 20° C. to 120° C., or between 20° C. to 110° C., or between 25° C. to 100° C., or between 40° C. to 100° C., or between 40° C. to 90° C. In certain embodiments the temperature at which the products are desorbed from the adsorbent is about 90° C.

In a particular embodiment of the invention, the pressure at which the products are adsorbed to the adsorbent is less than 200 psig (1,379 kPag), or less than 150 psig (1,034 kPag) or about 100 psig (689 kPag), or less than about 50 psig (345 kPag). In certain embodiments the pressure at which products are adsorbed to adsorbent is between 14.7 to 200 psig (101 to 1,379 kPag). Embodiments of the invention find particular application in the separation of organic products of gas fermentation such as acids, alcohols and diols from a generally aqueous fermentation broth. In particular acetic acid, ethanol and 2,3-butanediol are produced by fermentation of a gaseous substrate comprising CO and may be separated from an aqueous organic stream using the invention.

In further embodiments of the above aspects, an alcohol product such as ethanol is extracted from a portion of broth removed from the bioreactor (or another portion of broth) prior to the broth passing to the SMB module and optionally the filtration module. Preferably, the ethanol is extracted from the broth by distillation. In a particular embodiment, the extracted ethanol is used as a desorbent in the SMB module.

In further embodiments of the above aspects, the SMB module is regenerated following absorption of the products and/or acids. In a particular embodiment, the adsorbent is cleared of substantially all desorbent. In particular embodiments, the adsorbent is clear of desorbent by steam stripping. Steam stripping may occur either prior to adsorption to yield a condensed stripping solution that is removed from the system or in conjunction with the adsorption step where the condensed stripping solution is carried out of the system with the raffinate. The condensed stripping solution or desorbent-containing raffinate are distilled to recover extracted desorbent, which is returned to the process.

The gaseous substrate may comprise a gas obtained as a by-product of an industrial process. In certain embodiments, the industrial process is selected from the group consisting of ferrous metal products manufacturing, non-ferrous products manufacturing, petroleum refining processes, gasification of biomass, gasification of coal, electric power production, carbon black production, ammonia production, methanol production and coke manufacturing. In one embodiment of the invention, the gaseous substrate is syngas. In one embodiment, the gaseous substrate comprises a gas obtained from a steel mill.

In a particular embodiment, the gaseous substrate is a CO-containing gaseous substrate. In further embodiments, the substrate contains at least about 15% CO to 100% CO by volume, such as from 20% CO to 100% CO by volume, such as from 43% CO to 95% CO by volume, such as from 75% CO to 95% CO by volume, or such as from 80% to 90% CO by volume. In one particular embodiment, the gaseous substrate comprises approximately 95% CO. Lower CO levels, such as 6%, may be envisaged where the substrate also contains $CO_2$ and $H_2$. In other embodiments, the substrate stream comprises concentrations of $H_2$ from 2% to 13%.

In various embodiments, the fermentation is carried out using a microorganism culture comprising one or more strains of carboxydotrophic bacteria. In various embodiments, the carboxydotrophic bacterium is selected from *Clostridium, Moorella, Oxobacter, Peptostreptococcus, Acetobacterium, Eubacterium,* or *Butyribacterium*. In one embodiment, the carboxydotrophic bacterium is *Clostridium autoethanogenum*. In a particular embodiment, the bacterium has the identifying characteristics of accession number DSMZ10061 or DSMZ23693.

The invention also includes the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE FIGURES

These and other aspects of the present invention, which should be considered in all its novel aspects, will become apparent from the following description, which is given by way of example only, with reference to the accompanying figures, in which.

DETAILED DESCRIPTION OF THE INVENTION

Definitions

Unless otherwise specified, the following terms as used throughout this specification are defined as follows:

Raffinate—the matter remaining of the fermentation broth following the adsorption of fermentation products to the adsorbent.

Fermentation broth or broth—the mixture of components (including the broth culture and nutrient medium) found in the bioreactor.

Nutrient media—the solution added to the fermentation broth containing nutrients and other components appropriate for the growth of the microorganism culture.

Broth culture—the microorganism culture present in the fermentation broth.

Broth culture density—the density of microorganism cells in the fermentation broth.

Gaseous substrate comprising carbon monoxide—and like terms includes any gas which contains carbon monoxide. The gaseous substrate will typically contain a significant proportion of CO, preferably at least about 5% to about 100% CO by volume.

Acid—as used herein this term includes the carboxylic acid form. Acetic acid in its acetate form is not suitable for use with the adsorbent process of the present invention. Acetate present in the fermentation broth can be converted to the acid form by pH adjustment. The ratio of molecular acetic acid to acetate in the fermentation broth is dependent upon the pH of the system.

Bioreactor or fermenter—includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Moving Bed Biofilm Reactor (MBBR), Bubble Column, Gas Lift Fermenter, Membrane Reactor such as Hollow Fibre Membrane Bioreactor (HFMBR), Static Mixer, or other vessel or other device suitable for gas-liquid contact.

Second or secondary bioreactor—as used herein, these terms are intended to encompass any number of further bioreactors that may be connected in series or parallel with the first and/or second bioreactors.

Fermenting, fermentation process or fermentation reaction—and like terms as used herein, are intended to encompass both the growth phase and product biosynthesis phase of the process. In some embodiments the bioreactor may comprise a first growth reactor and a second fermentation reactor. As such, the treatment of or addition of components to, a fermentation reaction should be understood to relate to either or both of these reactors.

Partition ratio—as used herein is intended to define the ratio of the concentration of a substance in a single definite form, A, in the extract to its concentration in the same form in the other phase at equilibrium as shown in the following equation:

$$(K_D)_A = \frac{[A]_{org}}{[A]_{aq}}. \quad 1.$$

(IUPAC. Compendium of Chemical Terminology, $2^{nd}$ ed. (the "Gold Book"). Compiled by A. D. McNaught and A, Wilkinson, Blackwell Scientific Publications, Oxford (1997). XML on-line corrected version: hip://goldbook.iupac.org (2006) created by M. Nic, J. Jirat, B. Kosta; updates compiled by A. Jenkins. ISBN 0-9678550-9-8)

Component of a nutrient medium—as used herein is intended to define any substance provided in a liquid nutrient medium that supports the growth of a microorganism, including but not limited to vitamins, trace metals and minerals. Aqueous organic stream—as used herein is intended to define an aqueous stream comprising one or more organic products of a fermentation process. Examples of organic products include but are not limited to ethanol; 2,3-butanediol; acetic acid; propanol; Butanol; isopropanol and acetone, a compound that has a high affinity for water i.e., is highly soluble in water.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

The inventors have identified that SMB may have beneficial application to extracting organic compounds such as alcohols, diols, and organic acids that have a high affinity to water, from a generally aqueous solution and have developed processes therefor. Until now, SMB has only been used to separate organic compounds from organic solvents, or to extract organic compounds from aqueous solutions, where the organic component has a low affinity to water. Alcohols, diols, and organic acids have low carbon chain lengths and high polarity; therefore, such chemicals tend to have a high affinity for water i.e., are substantially completely soluble in water. Furthermore, these compounds are typically produced in low concentration solutions (i.e. below 10% w/w) containing impurities. Fermentation solutions often contain a variety of inorganic compounds as well as suspended and soluble biomass contaminants which limit adsorption by physically blocking or competing for the adsorbent surface. At least some preferred embodiments of the invention aim to overcome at least one of these limitations by providing a process and system with at least one of optimised adsorbent selectivity, capacity, mass transfer rate, and long-term stability. The invention also preferably provides an SMB module that has been optimised for continuous operation to reduce SMB capital expenditure and operating costs.

This method of coupling gas fermentation to SMB technology to extract fermentation products offers several advantages over known separation methods.

Regenerative, continuous adsorption reduces adsorbent and solvent/desorbent quantities and energy consumption. Operating costs are significantly lower than conventional unit operations such as distillation, solvent extraction and crystallization.

Relative to fixed beds, SMB has a much greater effective volume of functioning adsorbent. In a batch (fixed bed) process, liquid composition at a given bed level changes cyclically with time and large portions of the bed are not active at a given time. During continuous operation using SMB extraction the composition at a given level is fixed and the entire bed performs a useful function.

The fermentation products may be desorbed from the adsorbent by passing a desorbent/solvent over the adsorbent to yield a product-solvent solution. The invention has a further advantage over conventional separation techniques in that it separates organic products at high yield and purity, with minimal to no carry-over of solvent (for example water from the broth) and/or undesired solutes from the fermentation broth.

A further advantage of SMB is its ability to simultaneously extract more than one product from solution. Optimisation of the adsorbent bed allows SMB to cleanly extract multiple organic products under the same operating conditions, which cannot be done using conventional extraction methods.

In broad terms the invention provides a method of separation of one or more fermentation products from a fermentation broth using a simulated moving bed (SMB) module comprising an adsorbent.

Embodiments of the invention find particular application in the separation of aqueous organic products of gas fermentation such as acids, alcohols and diols from a fermentation broth. In particular acetic acid, ethanol and 2,3-butanediol are produced by fermentation of a gaseous substrate comprising CO and may be separated from the aqueous organic stream using the invention.

Known solvent extraction systems exhibit poor partition coefficients when used with broths having low organic product concentrations. While salt saturation can improve the partition coefficient, this adds to the cost of removing salts from the waste aqueous and dramatically increases consumable costs if the salts cannot be recovered for reuse. SMB requires minimum chemical consumption and broth treatment due to the selective adsorbtion/desorbtion of fermentation products thereby simplifying the extraction process. In particular embodiments of the invention, when the desorbent chemical used is an organic product from the fermentation, the SMB process requires substantially no chemical consumption.

In particular embodiments of the invention, the methods comprise the step of filtration of the fermentation broth prior to passing it to the SMB module. Filtration results in the removal of suspended and/or soluble biomass from the fermentation broth. Filtration may be by way of passing the broth through a membrane including but not limited to nanofiltration and ultrafiltration membranes, by denaturation of the fermentation broth, or by other methods of filtration known in the art. Flocculation can be induced by addition of a flocculent prior to filtration. Filtration may be carried out in a discrete module or be incorporated as part of the SMB module.

An example of a suitable adsorbent is a fluorinated carbon adsorbent. In certain embodiments the adsorbent is an activated carbon adsorbent or a fluorinated carbon adsorbent. In other embodiments the adsorbent is a C18 surface modified silica gel.

Preferably the adsorbent can be any adsorbent material capable of separating water from a denatured fermentation broth. Suitable adsorbents include fluorinated carbon adsorbents. Examples of suitable fluorinated carbon adsorbents include surface fluorinated carbon adsorbents such as ORSCNCB4FL5GR and ORSNCB4FLGR (available from Orochem Technologies, Inc.) and hereinafter referred to as FC-5 and FC-1 respectively. Other suitable adsorbents include activated carbon adsorbents. An example of an activated carbon adsorbent is ORSNCB4GR (available from Orochem Technologies, Inc, Lombard, Ill.) and hereinafter referred to as E-325. C18 surface modified silica gels also have suitable properties for use in the SMB process described herein. An exemplary C18 surface modified silica gel is RELIASIL 5 micron C18 (available from Infochroma, Zug, Switzerland).

By using an optimised adsorbent and conditions, the inventors have shown that the fermentation products may be extracted from the broth in an efficient way with high yield compared to conventional extraction techniques. An optimised hydrophobic adsorbent has been shown by the inventors to exhibit a high capacity and selectivity for organic compounds such as ethanol, propanol, butanol, acetic acid, 2,3-butanediol and acetone. The method also results in the substantially complete rejection of the water and inorganic salts present in solution.

In a particular embodiment, the adsorbent adsorbs at least approximately 50%, approximately 60%, approximately 70%, approximately 80%, approximately 90%, approximately 95%, approximately 99% or substantially 100% of the fermentation products from the broth.

Products may be separated from the desorbed product mixture by standard methods known to one of skill in the art such as distillation. For example, the boiling point of ethanol is 78.8° C. and that of acetic acid is 107° C. As a result, ethanol and acetic acid can readily be separated from each other using a volatility-based method such as distillation. Acetate may be recovered by adsorption on activated charcoal. Another example of separation is organo-solvent nanofiltration membranes. These enable the size separation of two (2) solvent components from each other through pressure filtration.

SMB requires a solvent desorbent to remove the organic product from the adsorbent. An appropriate desorbent ensures a clean separation from the adsorbent and subsequently from the desorbed product with only minor changes to process conditions, enabling near complete desorbent regeneration. Preferably the desorbent is selected from the group comprising methanol, ethanol, propanol, and methyl tertiary butyl ether. In preferred embodiments, the desorbent is methanol or ethanol.

In a particular embodiment, the solvent used for desorption is a solvent produced by the fermentation process and that has been previously extracted. This reduces consumables costs and possible waste treatment requirements. Using an extracted product as a solvent reduces the chance that undesirable solvent/desorbent or solvent/desorbent contaminants are recycled to the broth which can inhibit fermentation efficiency. In a particular embodiment, the solvent is ethanol that has been produced by the fermentation or a linked fermentation process. Such a solvent may be extracted from the removed portion of the broth prior to the broth passing to the SMB module or may be obtained from another portion of the both.

Because SMB relies on molecular interactions between the target product and the adsorbent surface, its separation performance does not require high temperatures, unlike distillation. SMB enables the continuous recovery of organic compounds from both hydrocarbon and aqueous solutions with no significant heat or pressure demand. This can reduce energy consumption and should also result in decreased greenhouse gas emissions. The lower temperature and pressure requirements may also avoid degeneration of broth nutrients enabling recycle of the raffinate with minimal treatment.

In a particular embodiment of the invention, the temperature at which the products are adsorbed to the adsorbent is between 25° C. to 75° C. In a preferred embodiment the temperature at which the organic products are adsorbed to the adsorbent is about 25° C. In a further particular embodiment of the invention, the temperature at which the products are desorbed from the adsorbent is between 25° C. to 120° C. In certain embodiments the temperature at which the products are desorbed from the adsorbent is about 90° C. In a particular embodiment of the invention, the pressure at which the products are adsorbed to the adsorbent is less than 200 psig (1,379 kPag) or less than 150 psig (1,034 kPag) or about 100 psig (689 kPag).

In an embodiment of the invention, the raffinate is recycled to the bioreactor. Before recycling, the raffinate may be treated and the treatment may consist of additional components or nutrients (such as B vitamins) being added to the raffinate to replenish the nutrient medium. The pH of the raffinate may be adjusted before being returned to the bioreactor to control the pH of the broth in the bioreactor.

The control of pH in a fermentation reaction is a critical factor that can affect a number of variables such as the reaction rate and product formed. Although the microorganisms involved in the fermentation will often produce products across a range of pH, maintaining an optimum pH for particular reaction conditions can maximise growth and/or production efficiency. The build-up of acids such as acetic acid and lactic acid can inhibit the fermentation and, if unchecked, can lead to collapse of the microorganism culture.

In broad terms, the invention also provides a method of controlling the pH of a fermentation broth in a bioreactor using a simulated moving bed (SMB) module comprising an adsorbent to remove a portion of the both, preferably said portion comprising an acid.

This method enables the pH of the fermentation broth to be continuously controlled without requiring the addition of acidifying or alkalising agents, or at least reducing the need therefor. This reduces consumable costs as well as reducing waste treatment that may be required to remove the agents.

In a further embodiment, the invention provides a method of controlling pH whereby the degree of adjustment of the pH of the broth is determined by the amount of one or more acids extracted from a removed portion of the broth.

In acid producing fermentations, acid accumulation within the bioreactor can lead to inhibition or collapse of the microbial culture. According to one aspect of the invention, an SMB module, can be used as an extended cell recycle system, allowing the return of essential biomass and soluble proteins, whilst stripping excess acids from the culture. In certain embodiments, substantially all acetic acid produced in the fermentation broth is removed through this process. In certain embodiments, where the pH in the bioreactor raises above a desired range, acetic acid can be returned to the reactor in the form of acetate. In certain embodiments, it is possible to control the pH in the bioreactor, by adjusting the amount of acid stripped from the broth stream as it passes through the SMB module. When the pH in the reactor drops below a desired level, more acid is stripped from the fermentation broth, to return the pH to a desire range. The pH of the bioreactor is dependent on the type of fermentation. In acetic acid fermentations, where acetic acid is the main fermentation product, the pH range should be maintained between around pH 6 to around pH 7.5. In alcohol fermentation, where one or more alcohols is the main fermentation product (aspects 1 and 2 of the present invention), the pH is maintained between around pH 4.5 to around pH 5.5. In certain embodiments the process is a continuous process.

Figure 1:
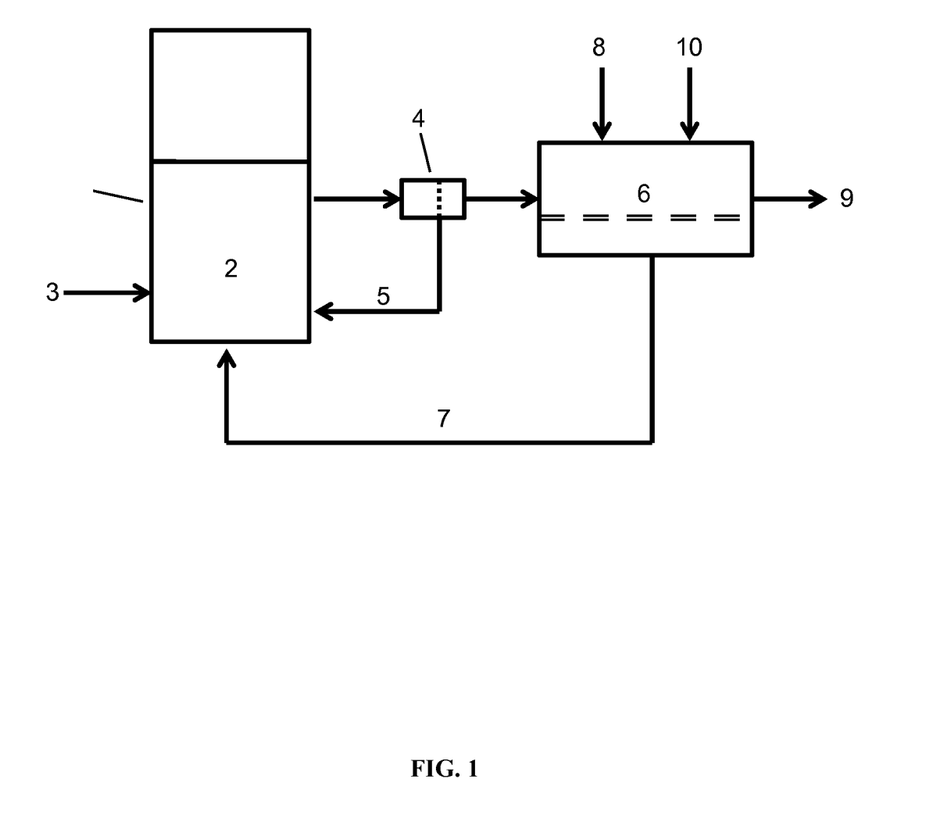
FIG. 1 is a schematic representation of a fermentation system according to an embodiment of the present invention.

The invention also provides a fermentation system an example embodiment of which is shown schematically in FIG. 1. The system comprises a bioreactor 1 containing a fermentation broth 2 containing microorganisms able to produce one or more fermentation products from a gaseous substrate 3 which may be fed to the bioreactor 1 via an appropriate inlet.

A portion of the broth 2 is fed from the bioreactor 1 to broth 2 via a filtration module 4 adapted to remove suspended and/or soluble biomass from the fermentation broth. The concentrated biomass removed may be recycled 5 to the bioreactor. The biomass depleted broth is passed to a simulated moving bed module 6 comprising an adsorbent adapted to adsorb the one or more fermentation products from the biomass depleted broth, resulting in a raffinate stream (filtered biomass depleted broth that is not adsorbed to the adsorbent). The raffinate is recycled 7 to the bioreactor 1. A desorbent 8 is passed over the adsorbent to desorb the fermentation products which are removed in a concentrated metabolite stream 9 which may be subjected to further separation steps. The adsorbent 6 is cleared of all remaining desorbent (or "regenerated"), either by steam stripping 10 prior to subsequent adsorption, or in conjunction with the adsorption step where it is carried out of the system with the raffinate. In one embodiment, the system described above and shown in FIG. 1 may be used to control pH by removal of fermentation product (e.g. acids) from the broth.

Figure 2:
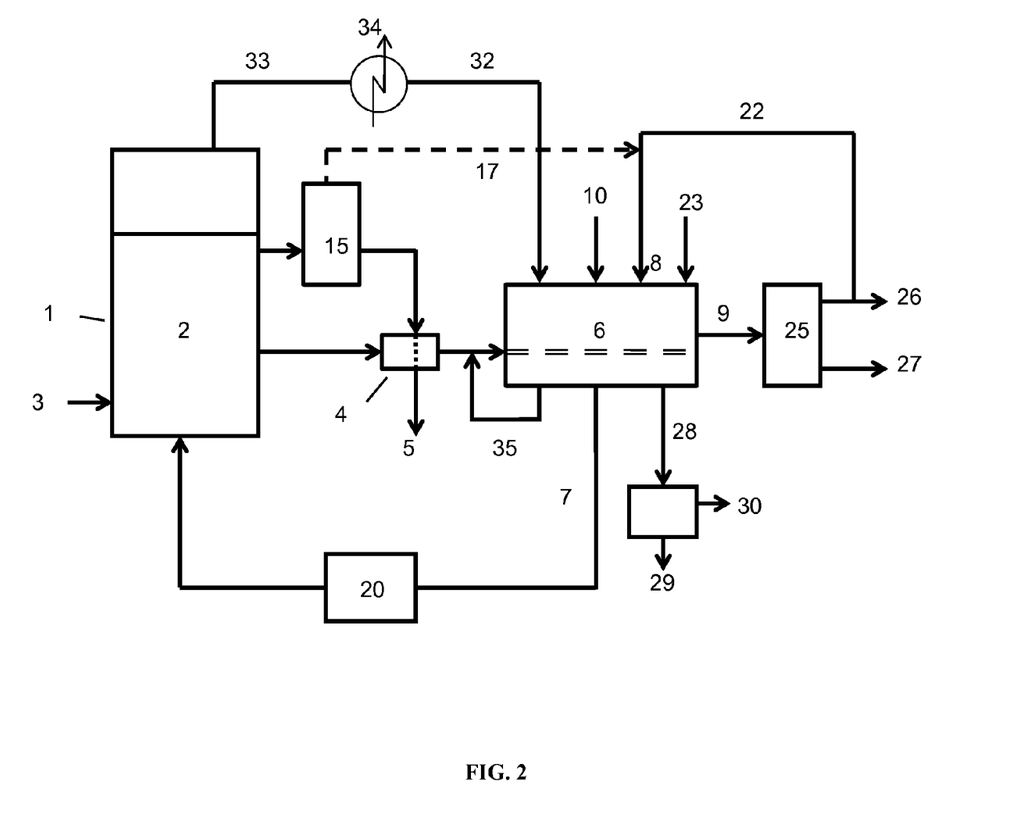
FIG. 2 is a schematic representation of a fermentation system according to an embodiment of the present invention whereby an SMB module is connected to a gas fermentation to extract fermentation products such as ethanol and 2,3-butanediol.

Another embodiment of the invention is shown schematically in FIG. 2. For ease of reference, like reference numerals have been used for like features. The system comprises a bioreactor 1 containing a fermentation broth 2 containing microorganisms able to produce one or more fermentation products from a gaseous substrate 3. A portion of the broth may be passed either a) directly to a filtration module 4 adapted to remove at least a portion of suspended and/or soluble biomass from the fermentation broth. Optionally volatile products such as ethanol are distilled 15 prior to being passed to the filtration module 4. The solid biomass is removed 15 from the filtration module 4 and may be disposed of or recycled to the fermentation broth. The distilled product may be passed 17 to the SMB module 6 to be used as a desorbent.

The biomass depleted broth is passed to the SMB module 6 comprising an adsorbent adapted to adsorb one or more fermentation products of the broth. The raffinate is recycled 7 to the bioreactor via a media preparation module 20 where treatment to optimise the media feed may occur. It will be appreciated that this module 20 may be added to the FIG. 1 embodiment.

A desorbent 8 is introduced to the SMB module 6 and passed over the adsorbent to desorb the fermentation products. The desorbent may be a fermentation product 17 or 22 such as ethanol or a consumable 23 such as methanol or water. Following desorption, fermentation products are removed in a concentrated metabolite stream 9 for further separation in a separation module 25 to yield purified products 26 and 27 such as ethanol and 2,3-butanediol respectively provided by way of example only. The desorbent is removed 28 along with waste vent gas 29 and the desorbent is collected 30 and may be recycled.

Steam 10 and heated vent gas 32 are used to regenerate the adsorbent. The heated vent gas is obtained by passing vent gas 33 from the bioreactor through a heat exchanger 34. Condensed steam and desorbent may be passed 35 to the biomass stripped broth for further processing.

In a particular embodiment, the gaseous substrate contains at least about 15% CO to 100% CO by volume, such as from 20% CO to 100% CO by volume, such as from 43% CO to 95% CO by volume, such as from 75% CO to 95% CO by volume, or such as from 80% to 90% CO by volume. In one particular embodiment, the gaseous substrate comprises approximately 95% CO. Lower CO levels, such as 6%, may be envisaged where the substrate also contains $CO_2$ and $H_2$. In other embodiments, the substrate stream comprises concentrations of $H_2$ from 2% to 13%.

While the description herein focuses on particular embodiments of the invention, namely the production of ethanol, 2,3-butanediol and/or acetic acid using CO as the primary substrate, it should be appreciated that the invention may be applicable to production of alternative alcohols or acids or alternative compounds. Additionally, the use of alternative substrates is envisaged including such substrates as will be known by persons of ordinary skill in the art to which the invention relates. For example, gaseous substrates containing carbon dioxide and hydrogen may be used. Further, the invention may be applicable to fermentation to produce butyrate, propionate, caproate, ethanol, propanol, and butanol. The methods may also be of use in producing hydrogen. By way of example, these products may be produced by fermentation using microbes from the genus *Moorella, Clostridia, Ruminococcus, Acetobacterium, Eubacterium, Butyribacterium, Oxobacter, Methanosarcina, Methanosarcina*, and *Desulfotomaculum*.

Simulated Moving Bed Separation

Simulated moving bed (SMB) is a separation technology based on adsorption and desorption of target organic solutes from solution. The technology was developed in the 1950's to purify industrial chemicals. SMB was adopted due to its five-fold increase in product throughput, with 10-fold reduction in energy demand, relative to fixed bed adsorptions. SMB development was accelerated by UOP for separation of organic components with similar boiling points and/or azeotropic properties (Sorbex™ and MX™ methods, for example). It has been found that optimisation of the adsorbent properties enables SMB to be used to extract organic fermentation products from aqueous fermentation broth solutions, where the organic component has a high affinity to water.

SMB operates continuously by fixing two or more columns containing adsorbent beds, while cycling and recycling a continuous stream of broth through the beds by use of multiport valves or a rotary valve fluid control. If elution across the total number of columns in series is not sufficient to extract the desired product(s) at the desired purity, the stream can be directed to pass through the columns additional times until adequate extraction is achieved. Thus the carefully timed switching of valves to re-direct the broth stream simulates the moving of the adsorbent beds. The remaining portion of the broth (comprising mainly water and salts) is termed the raffinate and may be removed for disposal or recycled.

The multi-pass approach of SMB has utility where affinity between compounds is high such as in the separation of chiral pharmaceuticals.

The SMB process consists of three main stages:

Adsorption Stage—Feed solution passes over adsorbent and the organic product adsorbs onto the surface. Resulting raffinate is removed from the system.

Desorption Stage—Desorbent solvent is passed over adsorbent, extracting the organic product from the surface, and the resulting solution removed for separation, typically via distillation.

Regeneration Stage—Adsorbent is cleared of all remaining desorbent, either via steam stripping prior to adsorption, or in conjunction with the adsorption step where it is carried out of the system with the raffinate. Condensed stripping solution or the desorbent-containing raffinate are distilled to recover extracted desorbent, which is returned to the process.

A rectification stage can be provided between the Adsoprtion stage, and the Desorption stage. During the rectification stage, at least a portion of the products on the adsorbent will travel down the surface of the adsorption column and collect at the bottom of the column. This allows less desorbent to be used in the desorption stage.

As will be appreciated by one of skill in the art, the simulated moving bed module referred to herein may comprise a number of different SMB designs. Exemplary SMB module designs that would be suitable for integration into the methods and systems of the present invention are described for example in U.S. Pat. Nos. 3,268,605, 3,706,812, 5,705,061 and 6,004,518, the entirety of which are incorporated herein by reference. Further apparatus that would be known to one of skill in the art may also be integrated into the SMB module to aid flow distribution (for example the apparatus described in U.S. Pat. No. 6,979,402) or provide other benefits.

While simulated moving bed systems are referred to herein, the invention is also intended to encompass the use of a fermentation coupled with actual moving bed systems such as that described in U.S. Pat. No. 6,979,402 B1 which rely on the same moving bed concept.

Fermentation

Certain embodiments of the invention are adapted to use gas streams produced by one or more industrial processes. Such processes include steel making processes, particularly processes which produce a gas stream having a high CO content or a CO content above a predetermined level (e.g. 5%). According to such embodiments, acetogenic bacteria are preferably used to produce acids and/or alcohols, particularly ethanol or butanol, within one or more bioreactors. Those skilled in the art will be aware upon consideration of the instant disclosure that the invention may be applied to various industries or waste gas streams, including those of vehicles with an internal combustion engine. Also, those skilled in the art will be aware upon consideration of the instant disclosure that the invention may be applied to other fermentation reactions including those using the same or different micro-organisms. It is therefore intended that the scope of the invention is not limited to the particular embodiments and/or applications described but is instead to be understood in a broader sense; for example, the source of the gas stream is not limiting, other than that at least a component thereof is usable to feed a fermentation reaction. The invention has particular application in improving the overall carbon capture and/or production of ethanol and other alcohols from gaseous substrates comprising CO. Processes for the production of ethanol and other alcohols from gaseous substrates are known. Exemplary processes include those described for example in WO2007/117157, WO2008/115080, WO2009/022925, WO2009/064200, U.S. Pat. Nos. 6,340,581, 6,136,577, 5,593,886, 5,807,722 and 5,821,111, each of which is incorporated herein by reference.

A number of anaerobic bacteria are known to be capable of carrying out the fermentation of CO to alcohols, diols and acids, and are suitable for use in present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091), *Clostridium ragsdalei* (WO/2008/028055) and *Clostridium autoethanogenum* (Abrini et al, Archives of Microbiology 161: pp 345-351). Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Moorella thermoacetica, Moorella thermoautotrophica, Ruminococcus productus, Acetobacterium woodii, Eubacterium limosum, Butyribacterium methylotrophicum, Oxobacter pfennigii, Methanosarcina barkeri, Methanosarcina acetivorans, Desulfotomaculum kuznetsovii* (Simpa et. al. Critical Reviews in Biotechnology, 2006 Vol. 26. Pp 41-65). In addition, it should be understood that other acetogenic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number 19630. In another embodiment, the *Clostridium autoethanogenum* has the identifying characteristics of DSMZ deposit number DSMZ 10061 or DSMZ23693. The laboratory strain of this bacterium is known as LZ1561.

In one embodiment, the microorganism is selected from the group of carboxydotrophic acetogenic bacteria. In certain embodiments the microorganism is selected from the group comprising *Clostridium autoethanogenum, Clostridium ljungdahlii, Clostridium ragsdalei, Clostridium carboxidivorans, Clostridium drakei, Clostridium scatologenes, Clostridium coskatii, Butyribacterium limosum, Butyribacterium methylotrophicum, Acetobacterium woodii, Alkalibaculum bacchii, Blautia producta, Eubacterium limosum, Moorella thermoacetica, Moorella thermautotrophica, Oxobacter pfennigii,* and *Thermoanaerobacter kiuvi*.

In one particular embodiment, the microorganism is selected from the cluster of ethanologenic, acetogenic Clostridia comprising the species *C. autoethanogenum, C. ljungdahlii,* and *C. ragsdalei* and related isolates. These include but are not limited to strains: *C. autoethanogenum* JAI-1$^T$ (DSM10061) [Abrini J, Naveau H, Nyns E-J: *Clostridium autoethanogenum*, sp. nov., an anaerobic bacterium that produces ethanol from carbon monoxide. Arch Microbiol 1994, 4: 345-351], *C. autoethanogenum* LBS1560 (DSM19630) [Simpson S D, Forster R L, Tran P T, Rowe M J, Warner I L: Novel bacteria and methods thereof. International patent 2009, WO/2009/064200], *C. autoethanogenum* LBS1561 (DSM23693), *C. ljungdahlii* PETC$^T$ (DSM13528=ATCC 55383) [Tanner R S, Miller L M, Yang D: *Clostridium ljungdahlii* sp. nov., an Acetogenic Species in *Clostridial* rRNA Homology Group I. Int J Syst Bacteriol 1993, 43: 232-236], *C. ljungdahlii* ERI-2 (ATCC 55380) [Gaddy J L: *Clostridium* stain which produces acetic acid from waste gases. 1997, U.S. Pat. No. 5,593,886], *C. ljungdahlii* C-01 (ATCC 55988) [Gaddy J L, Clausen E C, Ko C-W: Microbial process for the preparation of acetic acid as well as solvent for its extraction from the fermentation broth. 2002, U.S. Pat. No. 6,368,819], *C. ljungdahlii* O-52 (ATCC 55989) [Gaddy J L, Clausen E C, Ko C-W: Microbial process for the preparation of acetic acid as well as solvent for its extraction from the fermentation broth. 2002, U.S. Pat. No. 6,368,819], *C. ragsdalei* P11$^T$ (ATCC BAA-622) [Huhnke R L, Lewis R S, Tanner R S: Isolation and Characterization of novel *Clostridial* Species. International patent 2008, WO 2008/028055], related isolates such as "*C. coskatii*" [Zahn et al—Novel ethanologenic species *Clostridium coskatii* (US Patent Application number US20110229947)], or mutated strains such as *C. ljungdahlii* OTA-1 (Tirado-Acevedo O. Production of Bioethanol from Synthesis Gas Using *Clostridium ljungdahlii*. PhD thesis, North Carolina State University, 2010). These strains form a subcluster within the *Clostridial* rRNA cluster I, and their 16S rRNA gene is more than 99% identical with a similar low GC content of around 30%. However, DNA-DNA reassociation and DNA fingerprinting experiments showed that these strains belong to distinct species [Huhnke R L, Lewis R S, Tanner R S: Isolation and Characterization of novel *Clostridial* Species. International patent 2008, WO 2008/028055].

All species of this cluster have a similar morphology and size (logarithmic growing cells are between 0.5-0.7×3-5 ìm), are mesophilic (optimal growth temperature between 30-37° C.) and strictly anaerobe [Tanner R S, Miller L M, Yang D: *Clostridium ljungdahlii* sp. nov., an *Acetogenic* Species in *Clostridial* rRNA Homology Group I. Int J Syst Bacteriol 1993, 43: 232-236; Abrini J, Naveau H, Nyns E-J: *Clostridium autoethanogenum*, sp. nov., an anaerobic bacterium that produces ethanol from carbon monoxide. Arch Microbiol 1994, 4: 345-351; Huhnke R L, Lewis R S, Tanner R S: Isolation and Characterization of novel *Clostridial* Species. International patent 2008, WO 2008/028055]. Moreover, they all share the same major phylogenetic traits, such as same pH range (pH 4-7.5, with an optimal initial pH of 5.5-6), strong autotrophic growth on CO containing gases with similar growth rates, and a similar metabolic profile with ethanol and acetic acid as main fermentation end product, and small amounts of 2,3-butanediol and lactic acid formed under certain conditions. [Tanner R S, Miller L M, Yang D: *Clostridium ljungdahlii* sp. nov., an *Acetogenic* Species in *Clostridial* rRNA Homology Group I. Int J Syst Bacteriol 1993, 43: 232-236; Abrini J, Naveau H, Nyns E-J: *Clostridium autoethanogenum*, sp. nov., an anaerobic bacterium that produces ethanol from carbon monoxide. Arch Microbiol 1994, 4: 345-351; Huhnke R L, Lewis R S, Tanner R S: Isolation and Characterization of novel *Clostridial* Species. International patent 2008, WO 2008/028055]. Indole production was observed with all three species as well. However, the species differentiate in substrate utilization of various sugars (e.g. rhamnose, arabinose), acids (e.g. gluconate, citrate), amino acids (e.g. arginine, histidine), or other substrates (e.g. betaine, butanol). Moreover some of the species were found to be auxotroph to certain vitamins (e.g. thiamine, biotin) while others were not.

Culturing of the bacteria used in the methods of the invention may be conducted using any number of processes known in the art for culturing and fermenting substrates using anaerobic bacteria. By way of example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (v) J. L. Vega, et al. (1989). Study of gaseous substrate fermentations: Carbon monoxide conversion to acetate. 1. Batch culture. Biotechnology and Bioengineering. 34. 6. 774-784; (vi) J. L. Vega, et al. (1990). Design of Bioreactors for Coal Synthesis Gas Fermentations. Resources, Conservation and Recycling. 3. 149-160; all of which are incorporated herein by reference.

The fermentation may be carried out in any suitable bioreactors, such as one or more continuous stirred tank reactor (CSTR), immobilised cell reactor(s), a gas-lift reactor(s), bubble column reactor(s) (BCR), membrane reactor(s), such as a Hollow Fibre Membrane Bioreactor (HFMBR) or trickle bed reactor(s) (TBR). Also, in some embodiments of the invention, the bioreactor(s) may comprise a first, growth reactor in which the micro-organisms are cultured, and a second, fermentation reactor, to which fermentation broth from the growth reactor is fed and in which most of the fermentation product is produced. In particular embodiments, the second bioreactor is different to the first bioreactor.

According to various embodiments of the invention, the carbon source for the fermentation reaction is a gaseous substrate containing CO. The substrate may be a CO-containing waste gas obtained as a by-product of an industrial process, or from another source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing substrate may be captured from the industrial process before it is emitted into the atmosphere, using any convenient method. Depending on the composition of the CO-containing substrate, it may also be desirable to treat it to remove any undesired impurities, such as dust particles before introducing it to the fermentation. For example, the gaseous substrate may be filtered or scrubbed using known methods.

Alternatively, the CO-containing substrate may be sourced from the gasification of biomass. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use in the present invention.

The CO-containing substrate will typically contain a major proportion of CO, such as at least about 15% CO to 100% CO by volume, such as from 20% CO to 100% CO by volume, such as from 43% CO to 95% CO by volume, such as from 75% CO to 95% CO by volume, or such as from 80% to 90% CO by volume. In one particular embodiment, the gaseous substrate comprises approximately 95% CO. Lower CO levels, such as 6%, may be envisaged where the substrate also contains $CO_2$ and $H_2$. In other embodiments, the substrate stream comprises concentrations of $H_2$ from 2% to 13%.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of $H_2$:CO. In other embodiments, the substrate stream comprises concentrations of $H_2$ from 2% to 13%. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In particular embodiments, the substrate stream comprises CO2 and no or minimal CO.

Typically, the carbon monoxide will be added to the fermentation reaction in a gaseous state. However, the methods of the invention are not limited to addition of the substrate in this state. For example, the carbon monoxide can be provided in a liquid. For example, a liquid may be saturated with a carbon monoxide containing gas and that liquid added to the bioreactor. This may be achieved using standard methodology. By way of example a microbubble dispersion generator (Hensirisak et. al. Scale-up of microbubble dispersion generator for aerobic fermentation; *Applied Biochemistry and Biotechnology* Volume 101, Number 3/October, 2002) could be used for this purpose.

It will be appreciated that for growth of the bacteria and CO-to-product fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438, WO2007/117157, WO2008/115080, WO2009/022925, WO2009/058028, WO2009/064200, WO2009/064201 and WO2009/113878, referred to above.

The fermentation should desirably be carried out under appropriate conditions for the desired fermentation to occur (for example microbial growth and/or ethanol production). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition. Suitable conditions are described in WO02/08438, WO07/117,157, WO08/115,080 and WO2009/022925.

It is envisaged that the invention may comprise a system or method with additional control means and processing means such that parameters including media supply rates, liquid retention times and substrate supply rates can be controlled in accordance with the instant disclosure and methods known in the art, such as methods described in WO2010/093262, which are fully incorporated herein by reference.

The optimum reaction conditions will depend partly on the particular micro-organism used. However, in general, it is preferred that the fermentation be performed at pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

Also, since a given CO-to-ethanol conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per litre per day.

It is also desirable that the rate of introduction of the CO-containing gaseous substrate is such that the concentration of CO in the liquid phase does not become limiting. This is because a consequence of CO-limited conditions may be that acetic acid production increases and ethanol production decreases.

EXAMPLES

TABLE 1

Media composition

| Component | Final concentration mM/L |
|---|---|
| KCl | 25 |
| $CaCl_2 \cdot 2H_2O$ | 2 |
| $MgCl_2 \cdot 6H_2O$ | 2 |
| NaCl | 2 |
| $H_3PO_4$ | 5 |
| Metal solution [Table 2] | 20 mL |
| Vitamin solution [Table 3] | 20 mL |

TABLE 2

Trace metals solution

| Metal | Concentration mM/L stock solution |
|---|---|
| $FeCl_2 \cdot 4H_2O$ | 20 |
| $MnCl_2 \cdot 4H_2O$ | 0.4 |
| $CoCl_2 \cdot 6H_2O$ | 1.0 |
| $ZnCl_2$ | 1.0 |
| $H_3BO_3$ | 1.0 |
| $Na_2MoO_4 \cdot 2H_2O$ | 0.4 |
| $NiCl_2 \cdot 6H_2O$ | 0.4 |
| $Na_2SeO_3$ | 0.4 |
| $Na_2WO_4 \cdot 2H_2O$ | 0.4 |

TABLE 3

Vitamin solution

| Vitamin | Concentration mg/L stock solution (100x) |
| --- | --- |
| Thiamine hydrochloride (Vitamin B1) | 50 |
| Riboavin (Vitamin B2) | 50 |
| Nicotinic acid (Niacin or Vitamin B3) | 50 |
| Pantothenic acid (Vitamin B5) | 50 |
| Pyridoxine hydrochloride (Vitamin B6) | 10 |
| Biotin (Vitamin B7) | 20 |
| Folic acid (Vitamin B9) | 20 |
| 4-Aminobenzoic acid (PABA or Vitamin B10) | 50 |
| Cyanocobalamin (Vitamin B12) | 50 |
| Lipoic acid (Thioctic acid) | 50 |

Example 1

Fermentation for the Recovery of Fermentation Products

Media was prepared according to the composition described in Tables 1-3 to a volume of 1.5 L and 1.5 ml of resazurin added. The solution was heated and agitated whilst degassed with $N_2$. $ANa_2S$ drip was started at a rate of 0.1 ml/hr and temperature of the bioreactor set to 37° C. The pH was adjusted to 5.0 with $NH_4OH$ and chromium was added to adjust the ORP to −200 mV. The bioreactor was then supplied with RMG (43% CO, 20% CO2, 2.5% H2 and 33% N2) at a flow rate of 50 ml/min. The solution was inoculated with 150 ml of an actively growing *Clostridium autoethanogenum* culture. Once the reactor turned continuous, cell recycle was also initiated to give a bacterial dilution rate of 1.38 day$^{-1}$ and a media flow rate of 2.3 day$^{-1}$. During operation agitation (rpm) and gas flow (ml/min) were increased to maximise product concentrations. The fermentation was operated for a period of 8 days. Table 4 shows the metabolite concentrations in the liquid outflow of the bioreactor.

TABLE 4

Metabolite concentrations in outflow

| Time (days) | Acetate g/L | Ethanol g/L | 2,3-BDO g/L | Lactate g/L | Biomass g/L |
| --- | --- | --- | --- | --- | --- |
| 0.98 | 5.60 | 4.82 | 0.25 | 0.0 | 2.3 |
| 3.0 | 7.68 | 16.49 | 2.69 | 0.0 | 5.95 |
| 6.0 | 4.53 | 20.82 | 11.39 | 0.0 | 6.02 |

Example 2

Recovery of Fermentation Products from the Fermentation Broth

Pre-Treatment of Broth Stream

A 0.1 µm ceramic membrane cross flow filter (GE Healthcare Life Sciences Xampler Microfiltration Cartridge type) was used to remove the solid biomass/bacteria from the solution. After filtration, soluble biomass remains in the solution and must be minimised in order for the SMB to function correctly.

A 19 ml guard column containing activated carbon was tested for its capability to remove the remaining biomass and soluble proteins from the feed prior to testing in the SMB unit. The protein concentration of the solution was measured before the column and after the column using BCA analysis and the size distribution of the proteins before and after the guard column were assessed using SDS-PAGE analysis. Prior to passing through the guard column the protein concentration was approximately 1000 µg/ml and protein sizes were found to be 200 kDa, 70 kDa, 40 kDa, 30 kDa, and less than 2 kDa. The guard column was observed to remove 80% of the soluble proteins from the solution and the remaining proteins were found to be less than 2 kDa in size.

The guard bed was estimated to have adsorbed 4 g of proteins and other soluble biomass, such as DNA and enzymes. Five column volumes of methanol were used to desorb the proteins from the adsorbent bed and around 3.7 g of proteins were removed from the bed. A water backwash was used to desorb the DNA from the bed until DNA was no longer observed in the eluate.

Product Recovery

An 8-column SMB unit containing a fluorinated activated carbon solid phase was tested in conjunction with methanol as the solvent in order to separate ethanol, 2,3-butanediol and acetic acid from the fermentation product, treated as previously described. The feed contained 5% ethanol, 1% 2,3-butanediol, 0.8% acetic acid/acetate, with the remainder being water, media salts and metals used in the fermentation process. HPLC techniques were used to measure the composition of each stream exiting the SMB unit.

The flow rate of the feed solution was 11 ml/min and the flow rate of the desorbent was 11 ml/min. The step time was 12 minutes and the system was operated at a temperature of 75° C. The flow rate of the extract stream was optimised to give the best quality extract, i.e. minimal water content. 95.7% of the ethanol and 94.7% of the 2,3-butanediol from the feed exited the SMB through the extract stream. 41.7% of the acetic acid/acetate exited through the extract as acetic acid and 0.3% of the water from the feed was part of the extract. Three raffinate streams (Primary Raffinate, Secondary Raffinate I and Secondary Raffinate II) were produced in order to achieve streams suitable for recycle with minimal treatment. The flow rates of these raffinate streams were optimised to produce streams containing minimal metabolites; the optimised flow rates of the primary raffinate, secondary raffinate I and secondary raffinate II streams were 5.8 ml/min, 7.5 ml/min and 3.3 ml/min respectively. The primary raffinate stream contained 4.3% of the feed ethanol, 5.3% of the feed 2,3-butanediol and 57.9% of the feed water. 33.3% of the feed acetic acid/acetate was found in the primary raffinate stream in its acetate form. Secondary raffinate I contained 40.7% of the feed water and the remaining 25% of the acetic acid/acetate from the feed in its acetate form. Secondary raffinate II contained 0.1% of the feed water. 41.7% of the desorbent methanol was found in the extract stream, 30.7% in Secondary raffinate 1 and 28.5% in Secondary raffinate II.

pH Control

As the acetic acid/acetate can exit the SMB either through the extract or the raffinate streams depending on its form it is possible to influence its direction through pH adjustment of the solution prior to feeding the solution into the SMB. At a pH of about 5 there will be slightly more acetate present than acetic acid (the pKa for acetic acid is 4.74). In order to ensure that the acetic acid exits the SMB in its acetate form neutralisation of the solution is required; an increase in the solution's pH to pH7 or pH8 will significantly reduce the amount of acetic acid in the solution. Neutralisation was achieved through addition of sodium hydroxide to produce sodium acetate. In order for the acetic acid to exit in its acid form acidification to a pH close to pH2 is required and may be achieved through the addition of an acid.

The invention has been described herein with reference to certain preferred embodiments, in order to enable the reader to practice the invention without undue experimentation. Those skilled in the art will appreciate that the invention is susceptible to variations and modifications other than those specifically described. It is to be understood that the invention includes all such variations and modifications. Furthermore, titles, headings, or the like are provided to enhance the reader's comprehension of this document, and should not be read as limiting the scope of the present invention. The entire disclosures of all applications, patents and publications cited above and below, if any, are herein incorporated by reference.

More particularly, as will be appreciated by one of skill in the art, implementation of embodiments of the invention may include one or more additional elements. Only those elements necessary to understand the invention in its various aspects may have been shown in a particular example or in the description. However, the scope of the invention is not limited to the embodiments described and includes systems and/or methods including one or more additional steps and/or one or more substituted steps and/or systems and/or methods omitting one or more steps.

The reference to any prior art in this specification is not, and should not be taken as, an acknowledgement or any form of suggestion that that prior art forms part of the common general knowledge in the field of endeavour in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

What is claimed is:

1. A method for the production and recovery of ethanol and 2,3-butanediol from a mixture of fermentation products, the method comprising;
   a. flowing a gaseous substrate to a bioreactor containing a culture of one or more microorganisms in a liquid nutrient broth;
   b. fermenting the gaseous substrate to produce a fermentation broth comprising a mixture of fermentation products comprising ethanol and 2,3-butanediol;
   c. passing the fermentation broth to a treatment zone, wherein at least a portion of biomass and/or soluble proteins is removed from the fermentation broth to provide a treated stream;
   d. flowing the treated stream to a Simulated Moving Bed module comprising an adsorbent;
   e. adsorbing at least a portion of the ethanol and 2,3-butanediol from the treated stream to the adsorbent to yield a raffinate stream;
   f. passing a solvent through the adsorber to desorb the ethanol and 2,3-butanediol and provide an extract stream;
   g. passing the extract stream to a recovery zone operated at conditions to provide an ethanol stream and a 2,3-butanediol stream; and
   h. passing at least a portion of the raffinate stream back to the bioreactor.

2. The method of claim 1, wherein the treatment zone comprises a heat treatment zone.

3. The method of claim 1, wherein the adsorbent is selected from the group consisting of fluorinated carbon, activated carbon and modified C18 silica gel.

4. The method of claim 1, wherein the desorbent is selected from the group consisting of ethanol, methanol, propanol and methyl tertiary butyl ether.

5. The method of claim 2, wherein the treatment zone further comprises a filtration zone.

6. The method of claim 1, wherein one or more nutrients and/or trace elements are added to the raffinate stream prior to recycling the raffinate stream to the bioreactor.

7. The method of claim 1, wherein the microorganism is selected from the genus consisting of *Moorella, Clostridia, Ruminococcus, Acetobacterium, Eubacterium, Butyribacterium, Oxobacter, Methanosarcina, Desulfotomaculum*, and mixtures thereof.

* * * * *